(12) United States Patent
Nakamura et al.

(10) Patent No.: US 7,741,452 B2
(45) Date of Patent: *Jun. 22, 2010

(54) GLYCOSYLATION-DEFICIENT HEPATOCYTE GROWTH FACTOR

(75) Inventors: Toshikazu Nakamura, 1-4, Hoshojicho, Okazaki, Sakyo-ku, Kyoto-shi, Kyoto 606-8333 (JP); Kunio Matsumoto, Mino (JP); Kazuhiro Fukuta, Mino (JP)

(73) Assignee: Toshikazu Nakamura, Kyoto (JP)

(*) Notice: Subject to any disclaimer, the term of this patent is extended or adjusted under 35 U.S.C. 154(b) by 234 days.

This patent is subject to a terminal disclaimer.

(21) Appl. No.: 10/582,973

(22) PCT Filed: Dec. 15, 2004

(86) PCT No.: PCT/JP2004/018719

§ 371 (c)(1),
(2), (4) Date: Sep. 13, 2006

(87) PCT Pub. No.: WO2005/058951

PCT Pub. Date: Jun. 30, 2005

(65) Prior Publication Data

US 2007/0161549 A1   Jul. 12, 2007

(30) Foreign Application Priority Data

Dec. 16, 2003  (JP)  ............... 2003-418790
Dec. 22, 2003  (JP)  ............... 2003-425691

(51) Int. Cl.
*C07K 14/175* (2006.01)
(52) U.S. Cl. .................................... 530/399
(58) Field of Classification Search .............. None
See application file for complete search history.

(56) References Cited

U.S. PATENT DOCUMENTS

| 5,316,921 | A  | * | 5/1994  | Godowski et al. | ......... | 435/69.4 |
| 6,365,377 | B1 | * | 4/2002  | Patten et al.   | ........ | 435/91.1 |
| 7,125,688 | B2 | * | 10/2006 | Miyake et al.   | ........ | 435/69.1 |
| 7,129,064 | B2 | * | 10/2006 | Miyake et al.   | ........ | 435/69.1 |

FOREIGN PATENT DOCUMENTS

| JP | 7-508420 | 9/1995 |
| WO | 93/23541 | 11/1993 |

OTHER PUBLICATIONS

Shimizu et al., Biochemical and Biophysical Research Communications, 189(3):1329-1335.*

Fukuta et al., *Biochem. J.*, "Multiple biological responses are induced by glycosylation-deficient hepatocyte growth factor", vol. 388, pp. 555-562, 2005.
Stahl et al., *Biochem. J.*, "Functional and biophysical characterization of recombinant human hepatocyte growth factor isoforms produced in *Escherichia coli*", vol. 326, pp. 763-772, 1997.
Okigaki et al., *Biochemistry*, "Functional Characterization of Human Hepatocyte Growth Factor Mutants Obtained by Deletion of Structural Domains", vol. 31, No. 40, pp. 9555-9561, 1992.
Chirgadze et al., *FEBS Letters*, vol. 430, pp. 126-129, 1998.
R. Hofmann et al., "Scatter factor is a glycoprotein but glycosylation is not required for its activity," Biochim.Biophys..Act., 1992, 1120(3), pp. 343-350.
K. Miyazawa et al., "Human hepatocyte growth factor (hHGF), mRNA, complete cds.," Database GenBank accession No. M29145, Nov. 8, 1994.
K. M. Weidner et al., "Evidence for the identity of human scatter factor and human hepatocyte growth factor.," Proc. Natl. Acad. Sci. U.S.A., Aug. 1991, 88(16), pp. 7001-7005.
H. Hara et al., "Structural study of the N-linked oligosaccharies of hepatocyte growth factor by two-dimensional sugar mapping," J. Biochem. (Tokyo), 1993, vol. 114, No. 1, pp. 76-82.
P. Bellosta et al., "Cleavage of K-FGF produces a truncated molecule with increased biological activity and receptor binding affinity," The Journal of Cell Biology, vol. 121, 1993, pp. 705-713.
J. Aikawa et al., "Asparagine-linked glycosylation of the rat leukemia inhibitory factor expressed by simian COS7 cells,"Biosci. Biotechnol. Biochem., 1998, 62(7), pp. 1318-1325.
S. Bjoern et al., Human plasma and recombinant factor VII., Characterization of O-glycosylations at serine residues 52 and 60 and effects of site-directed mutagenesis of serine 52 to alanine.)), The Journal of Biological Chemistry, Jun. 1991, vol. 226, No. 17, pp. 11051-11057.
K. M. Davis-Fleische et al., "Site-directed Mutagenesis of Heparin-binding EGF-like Growth Factor (HB-EGF): Analysis of O-glycosylation Sites and Properties," Growth Factors, 2001, vol. 19, pp. 127-143.
K. Fukuda et al., "Functional Analysis of Suger Chains on HGF Based no Deglycosylation," Seikagaku, Aug. 2004, vol. 76, No. 8, p. 1035, 4P-214.
E. Adachi et al., "Functional Analysis of Sugar Chains on NK4 (HGF antagonist/angiogenesis inhibitor)," Seikagaku, Aug. 2004, vol. 76, No. 8, p. 1103, 4P-622.

* cited by examiner

*Primary Examiner*—Marianne P Allen
(74) *Attorney, Agent, or Firm*—Wenderoth, Lind & Ponack, L.L.P.

(57) ABSTRACT

The invention provides a modified glycosylation-deficient HGF and a production method thereof. The glycosylation-deficient HGF is produced by introducing amino acid mutation(s) so that no glycosylation take place at at least one glycosylation site of hepatocyte growth factor.

1 Claim, 6 Drawing Sheets

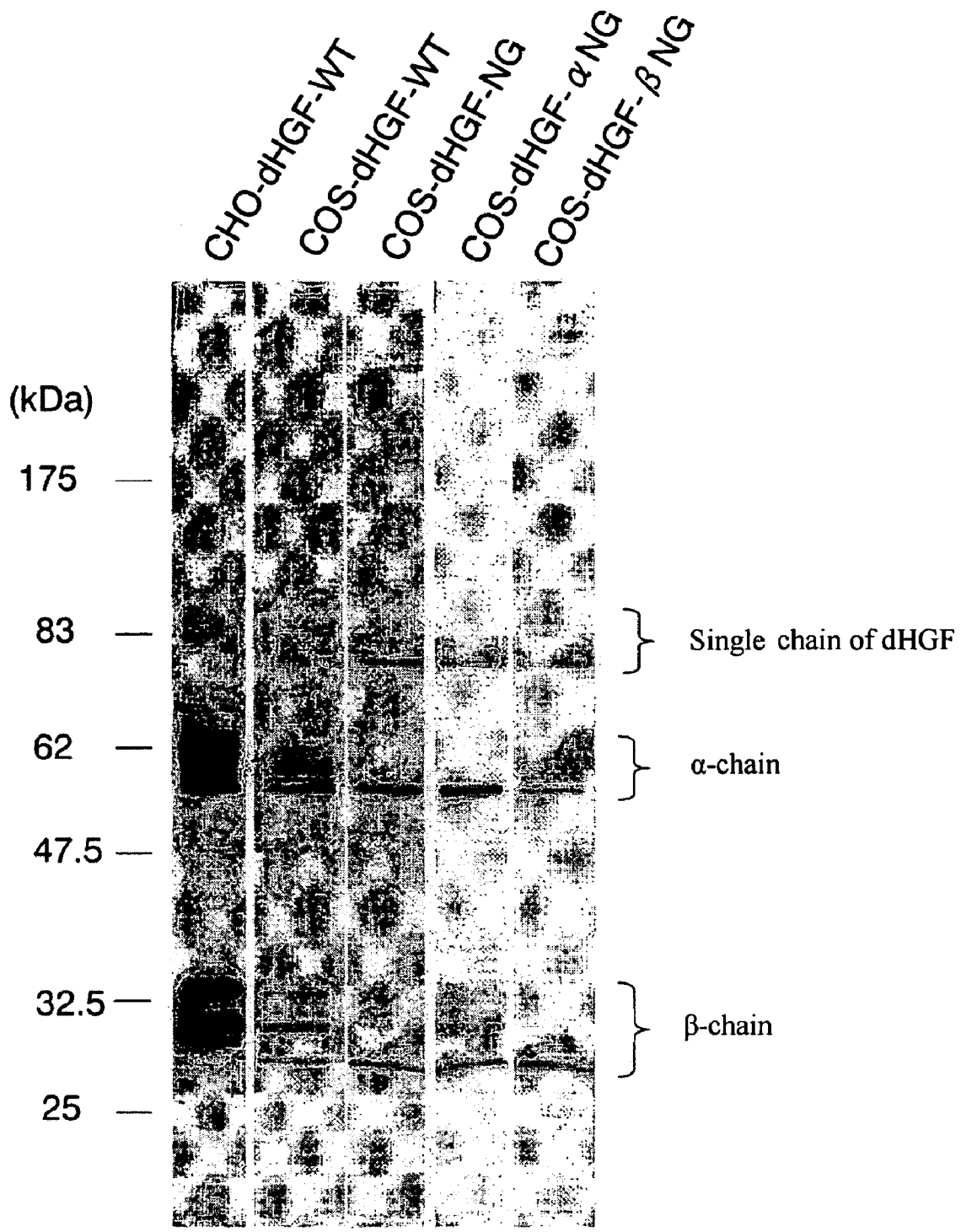
[Fig. 1]

[Fig. 2]
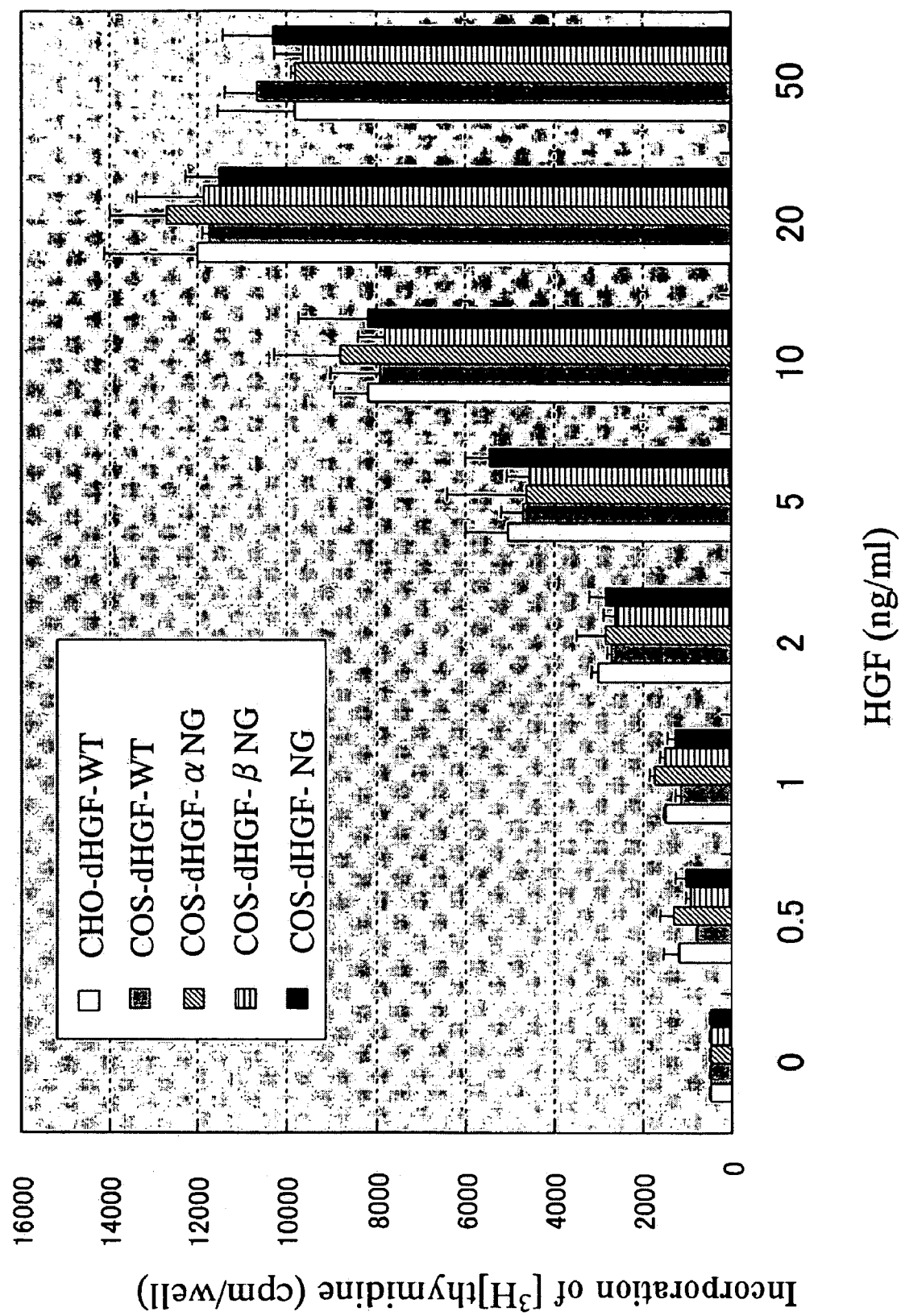

[Fig. 3]
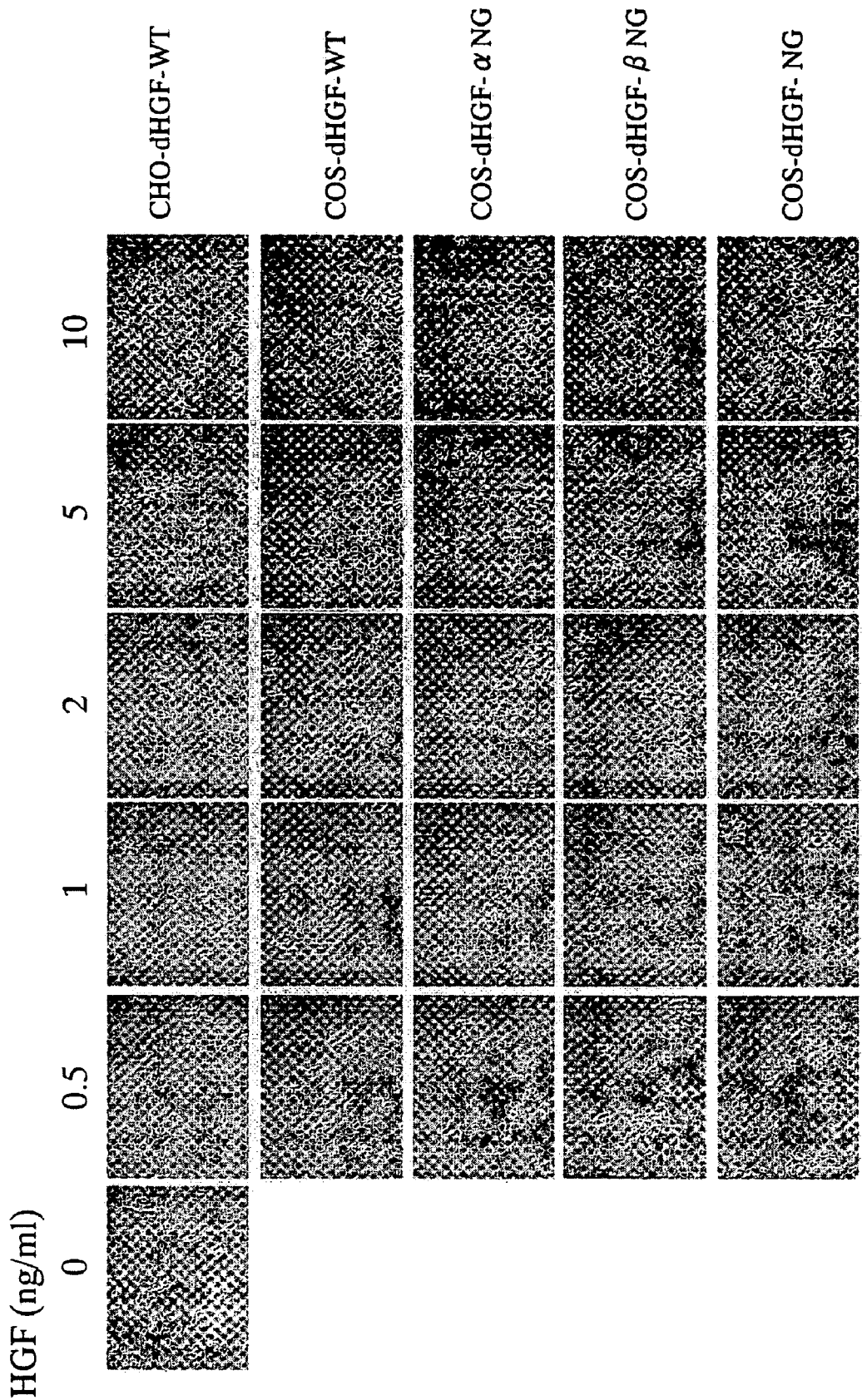

[Fig. 4]
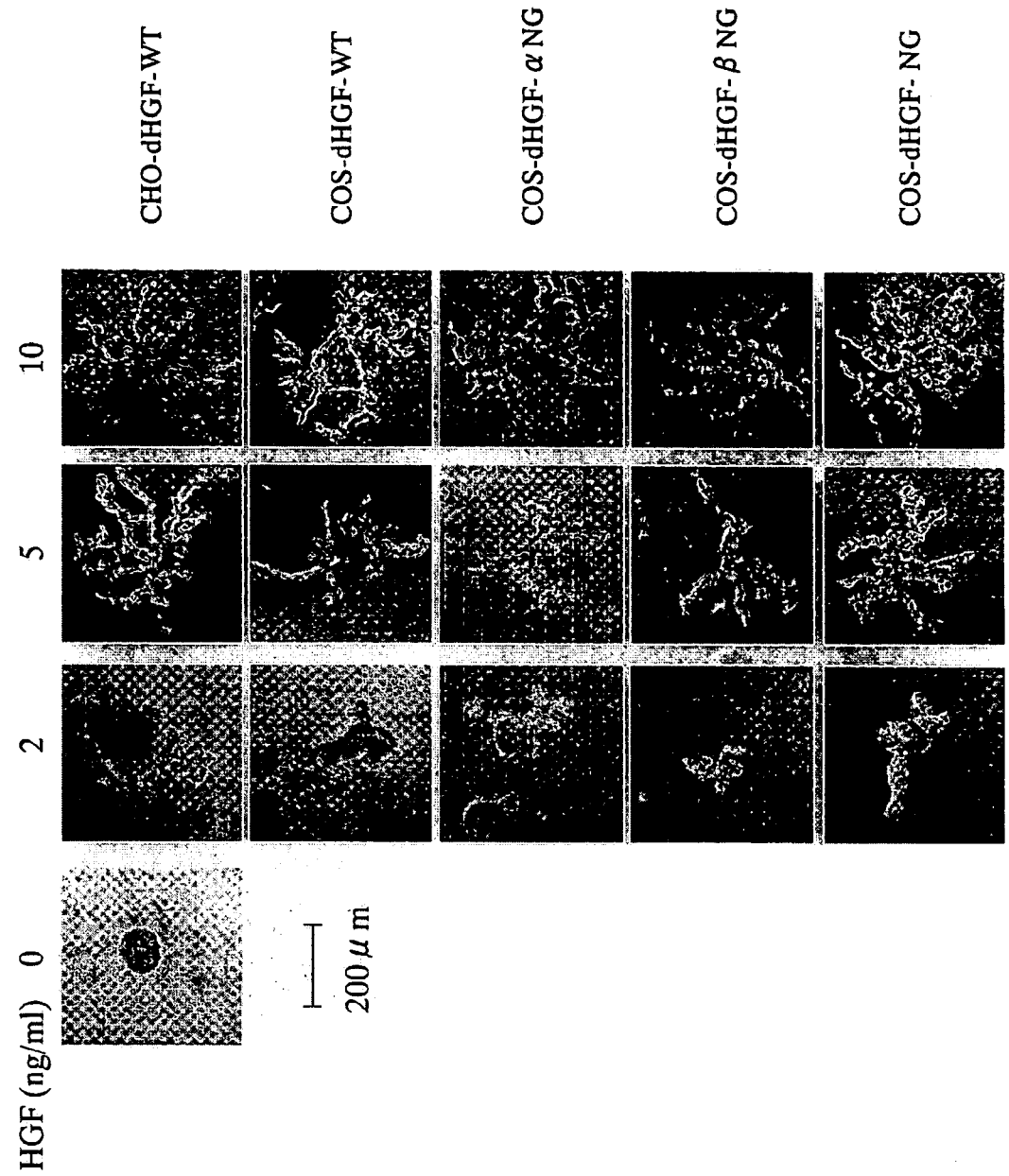

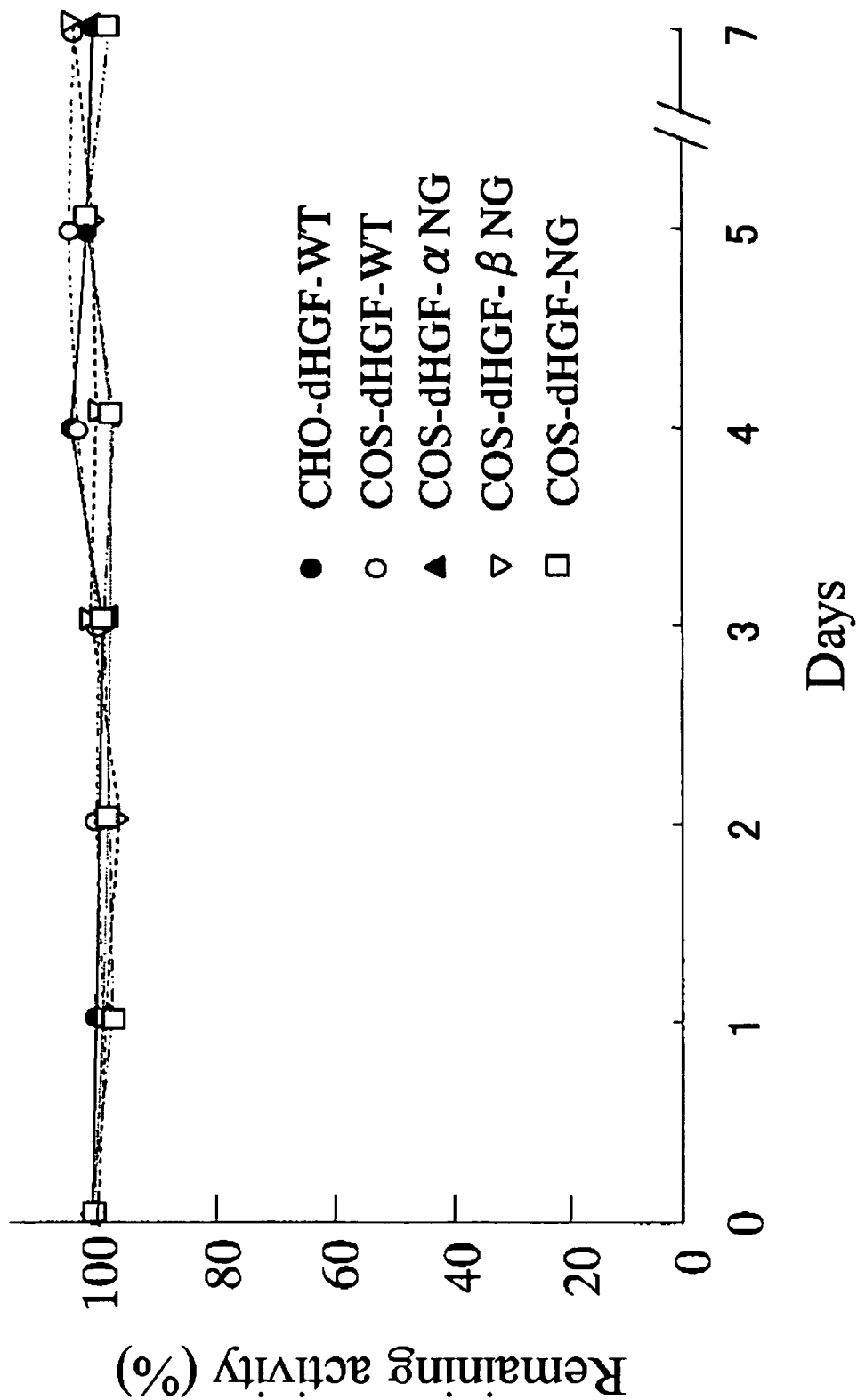
[Fig. 5]

[Fig. 6]
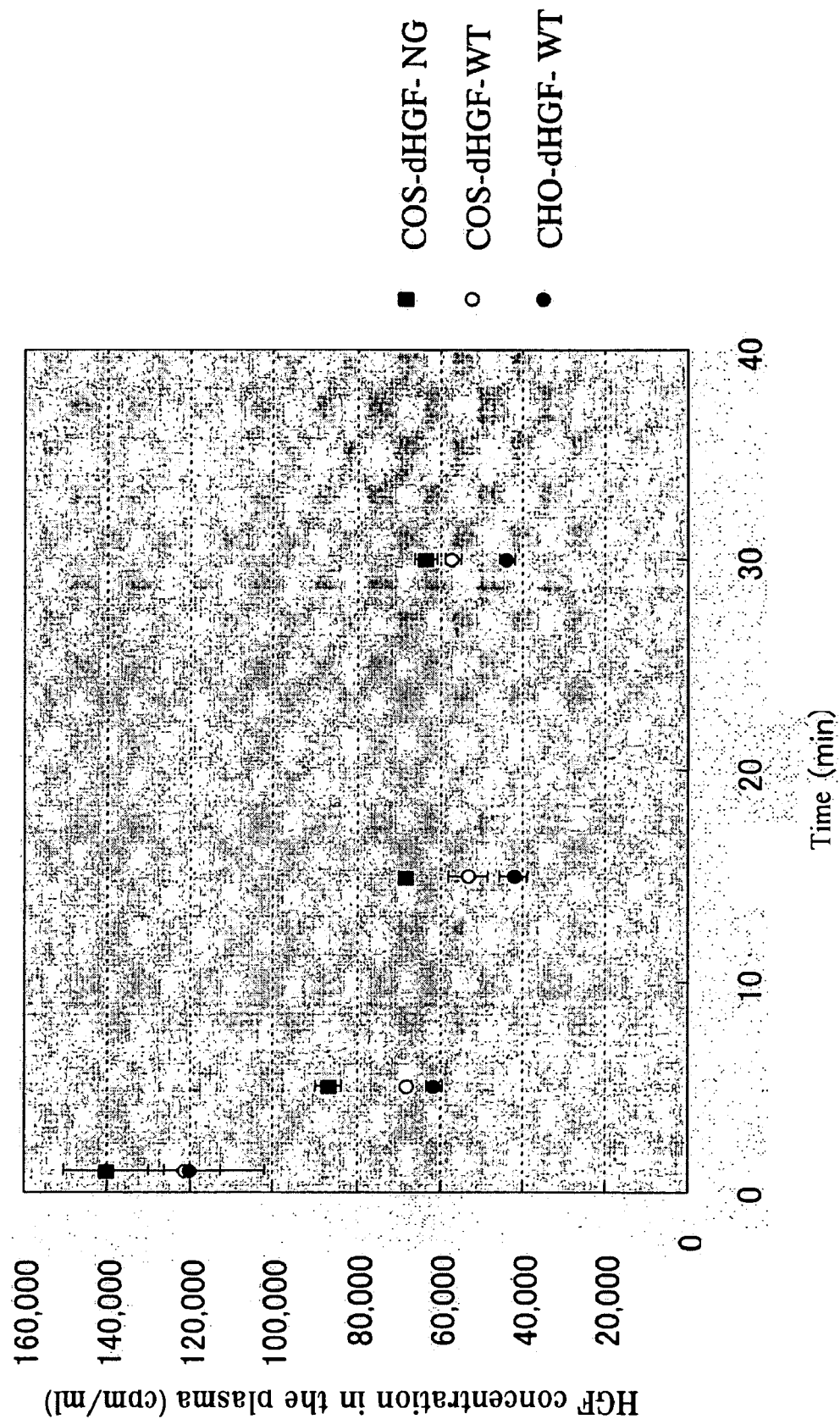

US 7,741,452 B2

GLYCOSYLATION-DEFICIENT HEPATOCYTE GROWTH FACTOR

This application is a U.S. national stage of International Application No. PCT/JP2004/018719 filed Dec. 15, 2004.

TECHNICAL FIELD

The invention relates to a glycosylation-deficient hepatocyte growth factor. In particular, the invention relates to hepatocyte growth factor that is modified by deficiency of glycosylation.

BACKGROUND ART

Hepatocyte growth factor (hereinafter abbreviated as HGF) is a protein having a mitogenic activity on hepatocytes. Some differences in amino acid sequences are observed among known HGFs and HGF is also named as SF (scatter factor), TCF (tumor cytotoxic factor) and the like in addition to HGF. The known proteins having mitogenic activities on hepatocytes are collectively named as HGFs in the present invention. HGFs are known to be physiologically active peptides that exert various pharmacological actions such as mitogenic action, morphogenetic action, neovascularization action, nerve protective action and anti-apoptotic action, in addition to mitogenic activity on hepatocytes (see non-patent document 1: Matsumoto, K. et al., Kidney International, 2001, vol. 59, p 2023-2038).

From its pharmacological actions, HGF is expected to be developed as therapeutic agents for cirrhosis, therapeutic agents for renal diseases, epithelial cell proliferation promoters, anti-cancer agents, preventive agents for side effects in cancer therapy, therapeutic agents for lung injury, therapeutic agents for gastroduodenal injuries, therapeutic agents for cerebral neuropathy, preventive agents for immunosuppression side effects, collagen degradation promoters, therapeutic agents for cartilage injury, therapeutic agents for artery diseases, therapeutic agents for pulmonary fibrosis, therapeutic agents for hepatic diseases, therapeutic agents for blood coagulation malfunction, therapeutic agents for plasma hypoproteinemia, therapeutic agent for wounds, neuropathy improving agents, hematopoietic stem cell increasing agents and hair restoration promoters (for example, see patent documents 1 to 14: JP-A-4-18028, JP-A-4-49246, EP-492614-A, JP-A-6-25010, WO93/8821, JP-A-6-172207, JP-A-7-89869, JP-A-6-40934, WO94/2165, JP-A-6-40935, JP-A-6-56692, JP-A-7-41429, WO93/3061 and JP-A-5-213721).

HGF is secreted from organs such as liver, brain, lung, bone marrow, spleen, placenta and kidney, or from blood cells such as platelets and leukocytes. However, since HGF is present in the body in a minute quantity, it is necessary to produce HGF in a large scale using cells by genetic engineering techniques in order to use it as medical preparations. It has been known that HGF can be produced using animal cells such as Chinese hamster ovary (CHO) cells (see, for example, patent documents 15 and 16: JP-11-4696-A and JP-10-191991-A).

However, the method for producing proteins using animal cells such as CHO cells is expensive, resulting in increase of drug prices.

As a method for producing a recombinant protein at a low cost, expression of proteins in prokaryotic cells such as E. coli by introducing genes of interest into them has been known (see non-patent document 2: Swarts, J. R., Current Opinion in Biotechnology, 2001, vol. 12, p 195-201). However, there exists a problem that no glycosylation occurs in recombinant proteins produced in the prokaryotic cells such as E. coli. This is because the prokaryotic cells such as E. coli do not contain endoplasmic reticulum and Golgi apparatus that are places for biosynthesis of sugar chain(s).

Addition of a sugar chain to a protein and its modification in an animal cell is post-translational modifications using no template, differing from the case of biosynthesis of DNAs or proteins. This post-translational modification is performed by a complicated mechanism mediated by various glycosylation-related enzymes locally present in intracellular organelle called endoplasmic reticulum and Golgi apparatus. That is, a sugar chain is elongated so as to obtain a given sugar chain structure when sequential addition and cleavage of monosaccharides occur according to a complicated biosynthetic pathway catalyzed by enzymes specific to certain linkages of monosaccharides (glycosidase and glycosyltransferase) (see non-patent document 3: Kornfeld, R., et. al, Annual Review of Biochemistry, 1985, vol. 54, p 631-664).

Sugar chain(s) added to proteins in this way have been known to be deeply involved in whole life phenomena of higher organisms (see non-patent documents 4 and 5: Kobata, A., European Journal of Biochemistry, 1992, vol. 209, p 483-501; Varki, A., Glycobiology, 1993, vol. 3, p 97-130).

It has been known that half or more of proteins in the human body exist as glycoproteins to which sugar chains are added (see non-patent document 6: Goochee, C. F. et al., Biotechnology, vol. 9, p 1347-1355).

If a glycoprotein originally present in the form carrying sugar chains is converted into a form containing no sugar chain, there is a fear of losing activity. For example, it is known that erythropoietin, known as a hematopoietic hormone, lose its activity when the sugar chains are removed (see non-patent document 7: Takeuchi, M. et al., Glycobiology, 1991, vol. 1, p 337-346).

Yeast is known as a host cell that is capable of producing a recombinant protein at low cost and has a glycosylation ability (see non-patent documents 8: Wiseman, A., Endeavor, 1996, vol. 20, p 130-132; non-patent document 9: Russell, C. et al., Australian Journal of Biotechnology, 1991, vol. 5, p 48-55; non-patent document 10: Buckholz, R. G. et al, Biotechnology, 1991, vol. 9, p 1067-1072). Since yeast is a eukaryotic cell and has endoplasmic reticulum and Golgi apparatus, it is consequently equipped with glycosylation mechanism. However, since the glycosylation mechanism of yeast differs significantly from that of animal cells, when a protein having glycosylation site(s) is produced in yeast, sugar chain(s) of yeast type would be added. It is known that the sugar chain structures of yeast are significantly different from those of human and other mammals (see non-patent document 11: Germmill, T. R. et al., Biochemica et Biophysica Acta, 1999, vol. 1426, p 227-237).

Accordingly, such recombinant proteins cannot be used for medicines for human beings and other mammals because they exhibit antigenicity against human and mammals.

Further, an insect cell is also a host having a glycosylation ability and can produce a protein at relatively low cost, however, the sugar chain structures of an insect cell are also different from those of human type (see non-patent document 12: Altmann, F. et al., Glycocomjugate Journal, 1999, vol. 16, p 109-123).

Accordingly, there is a possibility for a recombinant protein derived from insect cells to show antigenicity against human and other mammals.

Then, one can envisage production of a protein containing no sugar chains by removing sugar chains from a protein produced using yeast, insect cells, or the like, or by introducing a gene designed to have mutation(s) at glycosylation sites in a protein molecule into yeast, insect cells, or the like.

However, if a protein originally present in the form carrying sugar chains is converted into a protein containing no sugar chain, there is a fear of losing activity, as described above.

Five sugar chains are added to HGF (see non-patent documents 13: Hara, H. et al., Journal of Biochemistry, 1993, vol. 114, p 76-82; non-patent documents 14: Shimizu, N, et. al, Biochemical and Biophysical Research Communications, 1992, vol. 189, p 1329-1335). With respect to the influence of removing the sugar chains of HGF on the activity, it is reported that, when HGF-producing cells were cultured in the presence of tunicamycin, an inhibitor of N-glycosylation, secreted HGF maintained the motogenic activity (see non-patent document 15; Hofmann, R. et al., Biochemica et Biophysica Acta, 1992, vol. 1120, p 343-350. HFG is denoted as SF in the report).

However, this report does not give sufficient information since the extent of deficiency of the sugar chains in the HGF produced in the presence of tunicamycin was not analysed.

The report described that HGF maintained motogenic activity after treatment of the HGF with N-glycanase or O-glycanase, however, the report showed that HGF treated with N-glycanase or O-glycanase adsorbed onto a ConA column that recognizes sugar chains. The fact that HGF treated with N-glycanase or O-glycanase adsorbed onto a ConA column means that the removal of the sugar chains was limited. Therefore, the descriptions that the HGF treated with N-glycanase or O-glycanase maintained motogenic activity does not lead to a conclusion that glycosylation-deficient HGF maintains motogenic activity.

HGF has a variety of activities, including mitogenic activity, morphogenetic activity, neovascularization activity, anti-apoptotic activity and nerve protective activity in addition to the motogenic activity (see non-patent document 16: Matsumoto, K. et al., Biochemical and Biophysical Research Communications, 1997, vol. 239, p 639-644).

It cannot be always concluded that functions of HGF other than motogenic activity are maintained even if glycosylation-deficient HGF retains the motogenic activity. For example, NK2 that is a truncated variant of HGF has motogenic activity, whereas it has no mitogenic activity (see non-patent document 17: Hartmann, G. et al., Proceedings of National Academy of Science of the United States of America, 1992, vol. 89, p 11574-11578).

As can be seen from the above, it was unclear at all how many of the diverse functions are maintained in non-glycosylated HGF. HGF has been considered to be a repair factor of organs because of its diverse activities, and it could not be concluded that highly complicated functions are not affected by deficiency of sugar chains in HGF molecules.

DISCLOSURE OF THE INVENTION

The objects of the present invention are to provide a glycosylation-deficient hepatocyte growth factor in which sugar chains are allowed to be lacking, and to provide a method for producing the same.

The inventors of the present invention have found, through intensive studies on the function of the sugar chain to solve the problems above, that the functions of HGF are maintained even if the sugar chains of HGF are removed. It was quite unexpected that HGF, a highly functional protein, could maintain its function even if the sugar chains are removed. Moreover, it was an astonishing discovery that stability of glycosylation-deficient HGF in the blood circulation was improved as compared with glycosylated HGF. The inventors have completed the invention through advanced studies based on the findings described above.

The invention provides:

(1) a glycosylation-deficient hepatocyte growth factor lacking the sugar chains at all or at least one of the glycosylation sites of hepatocyte growth factor;

(2) the glycosylation-deficient hepatocyte growth factor according to the above (1), wherein a mutation is introduced into an amino acid sequence so that no glycosylation occurs at at least one of glycosylation sites of the hepatocyte growth factor;

(3) the glycosylation-deficient hepatocyte growth factor according to the above (2), wherein at least one of the following modifications of (a) to (d) are applied to the amino acid sequence of the hepatocyte growth factor:

(a) Asn in at least one of consensus sequences for N-glycosylation represented by Asn-X-Ser or Asn-X-Thr (X represents an amino acid except Pro), which exist in the amino acid sequence of hepatocyte growth factor, is substituted by another amino acid residue;

(b) Ser or Thr in one consensus sequence, or Ser and/or Thr in two or more consensus sequences for N-glycosylation represented by Asn-X-Ser or Asn-X-Thr (X represents an amino acid except Pro), which exist in the amino acid sequence of hepatocyte growth factor, is/are substituted by other amino acid residue(s), (c) X in at least one of consensus sequences for N-glycosylation represented by Asn-X-Ser or Asn-X-Thr (X represents an amino acid except Pro), which exist in the amino acid sequence of hepatocyte growth factor, is substituted by Pro, or (d) at least one of Ser and/or Thr that undergo/undergoes O-glycosylation, which exist in the amino acid sequence of hepatocyte growth factor, is/are substituted by other amino acid residue(s);

(4) the glycosylation-deficient hepatocyte growth factor according to any one of the above (1) to (3), wherein the hepatocyte growth factor is human hepatocyte growth factor;

(5) the glycosylation-deficient hepatocyte growth factor according to any one of the above (1) to (3), wherein the hepatocyte growth factor is feline or canine hepatocyte growth factor;

(6) the glycosylation-deficient hepatocyte growth factor according to any one of the above (1) to (4), which is modified based on the amino acid sequence of SEQ ID NO: 1, wherein at least one of modifications represented by (a) to (e) below is applied to the amino acid in SEQ ID NO: 1:

(a) substitution of amino acid 294 and/or 296 by another amino acid, and/or substitution of amino acid 295 by Pro, leading thereby to no glycosylation of the amino acid 294;

(b) substitution of amino acid 402 and/or 404 by another amino acid, and/or substitution of amino acid 403 by Pro, leading thereby to no glycosylation of the amino acid 402;

(c) substitution of amino acid 476 by another amino acid, resulting in no glycosylation of the amino acid 476;

(d) substitution of amino acid 566 and/or 568 by another amino acid, and/or substitution of amino acid 567 by Pro, leading thereby to no glycosylation of the amino acid 566; or (e) substitution of amino acid 653 and/or 655 by another amino acid, and/or substitution of amino acid 654 by Pro, leading thereby to no glycosylation of the amino acid 653;

(7) the glycosylation-deficient hepatocyte growth factor according to any one of the above (1) to (4), which is modified based on the amino acid sequence of SEQ ID NO: 2, wherein at least one of modifications represented by (a) to (e) below is applied to the amino acid in SEQ ID NO: 2:

(a) substitution of amino acid 289 and/or 291 by another amino acid, and/or substitution of amino acid 290 by Pro, leading thereby to no glycosylation of the amino acid 289;

(b) substitution of amino acid 397 and/or 399 by another amino acid, and/or substitution of amino acid 398 by Pro, leading thereby to no glycosylation of the amino acid 397;

(c) substitution of amino acid 471 by another amino acid, leading thereby to no glycosylation of the amino acid 471;

(d) substitution of amino acid 561 and/or 563 by another amino acid, and/or substitution of amino acid 562 by Pro, leading thereby to no glycosylation of the amino acid 561; or (e) substitution of amino acid 648 and/or 650 by another amino acid, and/or substitution of amino acid 649 by Pro, leading thereby to no glycosylation of the amino acid 648;

(8) a DNA comprising a base sequence encoding the glycosylation-deficient hepatocyte growth factor according to any one of the above (1) to (7);

(9) a vector integrated with the DNA according to the above (8);

(10) a method for producing the glycosylation-deficient hepatocyte growth factor according to any one of the above (1) to (7) comprising the steps of: introducing the vector according to the above (9) into a cell; culturing the cell; producing a glycosylation-deficient hepatocyte growth factor in the cell or into the cell culture medium; and recovering and purifying the glycosylation-deficient hepatocyte growth factor from the cell or from the cell culture medium;

(11) the method according to the above (10) for producing the glycosylation-deficient hepatocyte growth factor, wherein the cell is a eukaryotic cell;

(12) the method according to the above (11) for producing the glycosylation-deficient hepatocyte growth factor, wherein the eukaryotic cell is a yeast or an insect cell;

(13) a method for producing the glycosylation-deficient hepatocyte growth factor according to any one of the above (1) to (7), comprising the steps of: introducing the vector according to the above (9) into an insect individual, allowing the insect individual to produce the glycosylation-deficient hepatocyte growth factor, and recovering and purifying the glycosylation-deficient hepatocyte growth factor from the insect individual;

(14) a method for producing the glycosylation-deficient hepatocyte growth factor according to any one of the above (1) to (7), comprising the steps of: removing the sugar chain(s) wholly or partially by treating hepatocyte growth factor having sugar chain(s) with an enzyme, and recovering and purifying the glycosylation-deficient hepatocyte growth factor from the enzyme reaction solution;

(15) a method for producing the glycosylation-deficient hepatocyte growth factor according to any one of the above (1) to (7), comprising the steps of: introducing a vector integrated with a DNA containing a base sequence encoding hepatocyte growth factor having sugar chain(s) or the vector according to the above (9) into a cell having no glycosylation ability; culturing the cell; allowing the cell to produce a glycosylation-deficient hepatocyte growth factor in the cell or into the cell culture medium; and recovering and purifying the glycosylation-deficient hepatocyte growth factor from the cell or cell culture medium;

(16) a method for producing the glycosylation-deficient hepatocyte growth factor according to any one of the above (1) to (7), comprising the steps of: synthesizing the glycosylation-deficient hepatocyte growth factor by a cell-free protein synthesis system using a gene comprising a base sequence encoding hepatocyte growth factor having sugar chain(s) or the base sequence according to the above (8) as a template, and recovering and purifying the glycosylation-deficient hepatocyte growth factor from the reaction solution;

(17) a pharmaceutical preparation comprising the glycosylation-deficient hepatocyte growth factor according to any one of the above (1) to (7) as an active ingredient; and

(18) a gene therapy agent containing the DNA according to the above (8).

The glycosylation-deficient HGF of the present invention has characteristics identical to HGF having sugar chains with respect to mitogenic, motogenic and morphogenetic activities, and heat stability. Therefore, it can be used as a substitute for glycosylated HGF. Accordingly, the pharmaceutical preparation comprising the glycosylation-deficient HGF of the present invention as an active ingredient can be used similarly to glycosylated HGF, i.e., as therapeutic agents for cirrhosis, therapeutic agents for renal diseases, epithelial cell proliferation promoters, anti-cancer agents, preventive agents for side effects in cancer therapy, therapeutic agents for lung injury, therapeutic agents for gastroduodenal injuries, therapeutic agents for cerebral neuropathy, preventive agents for immunosuppression side effect, collagen decomposition promoters, therapeutic agents for cartilage injury, therapeutic agents for artery diseases, therapeutic agents for pulmonary fibrosis, therapeutic agents for hepatic diseases, therapeutic agents for blood coagulation malfunction, therapeutic agents for plasma hypoproteinemia, therapeutic agent for wound, neuropathy improving agents, hematopoietic cell increasing agents and hair restoration promoters for mammals (such as human, dog, cat, rat, mouse, rabbit, horse, cattle, sheep and guinea pig).

Medicines containing the DNA encoding the glycosylation-deficient HGF of the present invention can be also used as a gene therapy agent for the diseases as described above.

Since the glycosylation-deficient HGF of the invention is more stable in the blood circulation than glycosylated HGF, the dosage of HGF can be reduced to prevent the side effect of HGF.

The glycosylation-deficient HGF of the invention can be produced at low cost since it can be produced in yeast and insect cells.

BRIEF EXPLANATION OF THE DRAWINGS

FIG. 1 shows the results of SDS-PAGE analysis of each HGF. Reduced samples of HGFs were electrophoresed and the gel was subjected to silver staining.

FIG. 2 shows a graph of mitogenic activity of HGFs on hepatocytes, where the activity is indicated in terms of DNA synthesis of rat hepatocytes.

FIG. 3 shows motogenic activity of HGFs, where the activities were compared based on the degree of scattering of MDCK cells.

FIG. 4 shows motogenic activity of HGFs, where the activities were compared based on the degree of tube formation of MDCK cells.

FIG. 5 shows thermal stability of HGFS. Each HGF was incubated at 37° C. for the days indicated. The remaining activity was expressed as relative activity based on the amount of DNA synthesis of rat hepatocytes.

FIG. 6 shows stability of HGFs in the blood circulation.

BEST MODE FOR CARRYING OUT THE INVENTION

The present invention will be described in detail below.

The glycosylation-deficient HGF of the present invention refers to HGF that is modified so as to lack sugar chain(s) at the whole or at least one of the glycosylation sites of HGF having sugar chains derived from mammals such as human, dog, cat, rat, mouse, rabbit, horse, cattle, sheep and guinea pig.

Furthermore, the glycosylation-deficient HGF of the present invention includes proteins having an amino acid sequence in which a mutation is introduced so that the known HGFs do not undergo glycosylation, wherein one or several amino acids are deleted, substituted, added or inserted, and having an HGF activity. In addition, the glycosylation-deficient HGF of the present invention also includes proteins having a homology of at least about 60% or more, preferably about 80% or more, more preferably about 90% or more, and furthermore preferably about 95% or more with the amino acid sequence in which a mutation is introduced so that no glycosylation takes places in the known HGFs, and having an HGF activity.

The phrase "one or several amino acids are deleted, substituted, added or inserted" with respect to the amino acid sequence refers to deletion, substitution, addition or insertion of amino acid(s) of a number, one to several, which can be introduced by well-known technological methods such as a site-directed mutagenesis method or can be introduced naturally.

The term "homology" with respect to the amino acid sequence as described above refers to the degree of identity of amino acid residues constituting each sequence as a result of comparison of primary structures of proteins.

The glycosylation-deficient HGF of the invention can be obtained by introducing a vector, to which a mutation is introduced so that no glycosylation occurs at at least one site of the glycosylation sites of the HGF, into cells.

The glycosylation-deficient HGF of the invention may also be obtained by introducing a vector containing a base sequence of HGF having glycosylation sites into a cell with no glycosylation ability.

As the method of introducing mutation(s) into an HGF gene so as to prevent addition of sugar chain(s) at at least one of glycosylation sites of HGF, it is advantageous to introduce mutation(s) into a base sequence corresponding to the amino acid sequence of a glycosylation site to be deficient. Since the sugar chain attached to a protein includes an N-linked type and an O-linked type, the following mutations are introduced into a base sequence, respectively.

Consensus sequence for the attachment of N-linked sugar chains have been known (Asn-X-Ser or Asn-X-Thr; X represents an amino acid other than proline). When the consensus sequence exists, a sugar chain is added to Asn in the consensus sequence (Kobata A., Eur. J. Biochem., 1992, vol. 209, p. 483-501). Accordingly, an N-linked type sugar chain can be made deficient by introducing mutation(s) into a base sequence so as to convert Asn in the consensus sequence into another amino acid (for example Gln), or to convert Ser or Thr in the consensus sequence into another amino acid (for example Gly or Ala). In this case, it is preferable to appropriately select an amino acid for conversion so as not to form a new consensus sequence with backward and forward amino acids of the above-mentioned consensus sequence. It may also be permissible to introduce mutation(s) into a base sequence so that proline is introduced at X site in a consensus sequence.

In the case of an O-linked type sugar chain, a sugar chain is added to a hydroxyl group of Ser or Thr in an O-glycosylation site, however, a consensus sequence for O-glycosylation does not exist. A sugar chain at the O-glycosylation site can be made deficient by introducing mutation(s) into a base sequence so as to convert Ser or Thr subjected to O-glycosylation into another amino acid (for example, Gly and the like).

In this case, it is preferable to appropriately select an amino acid for conversion so as not to form the above-described consensus sequence for N-linked sugar chains with backward and forward amino acid sequences of the replaced amino acid.

The glycosylation sites, for example in the human HGF, are Asn at position 294 (N-linked type sugar chain), Asn at position 402 (N-linked type sugar chain), Thr at position 476 (O-linked type sugar chain), Asn at position 566 (N-linked type sugar chain) and Asn at position 653 (N-linked type sugar chain) of the amino acid sequence of SEQ ID NO: 1 in the sequence listing. The glycosylation sites in the 5 amino acids-deficient human HGF of SEQ ID NO: 2 in the sequence listing are Asn at position 289 (N-linked type sugar chain), Asn at position 379 (N-linked type sugar chain), Thr at position 471 (O-linked type sugar chain), Asn at position 561 (N-linked type sugar chain) and Asn at position 648 (N-linked type sugar chain).

The consensus sequence for N-linked sugar chains in the case of the human HGF is present at positions 294 to 296, positions 402 to 404, positions 566 to 568 and positions 653 to 655 of the amino acid sequence of SEQ ID NO: 1 in the sequence listing. The consensus sequence in the case of the 5-amino acids-deleted type human HGF is present at positions 289 to 291, positions 397 to 399, positions 561 to 563 and positions 648 to 650 of the amino acid sequence in SEQ ID NO: 2 in the sequence listing.

Introduction of mutation(s) into a base sequence of HGF can be conducted using a known technology such as the Kunkel method with synthetic mutagenic primers corresponding to a portion into which mutations are to be introduced. By using a commercially available mutagenesis kit and the like, mutations can be introduced easily.

A recombinant expression vector for glycosylation-deficient HGF can be constructed from a recombinant vector such as a plasmid and a phage, which contains DNA coding an amino acid sequence of glycosylation-deficient HGF or DNA coding the amino acid sequence of HGF having sugar chain(s), by excising this DNA with a restriction enzyme, and re-connecting it to downstream of a promoter within a vector suitable for expression of the glycosylation-deficient HGF by using a restriction enzyme and DNA ligase. More specifically, the vector is constructed so that it contains, if necessary, (1) promoter, (2) ribosome binding site, (3) initiation codon, (4) DNA containing a base sequence coding a glycosylation-deficient HGF of the present invention, (5) termination codon and (6) terminator in this order toward downstream direction of transcription.

The above-mentioned DNA includes not only DNA composed of a base sequence coding a glycosylation-deficient HGF that can be obtained by introducing mutation(s) into the above-mentioned glycosylation site(s), but also (a) DNA having a base sequence having deletion, substitution, addition or insertion of one or more bases in the base sequence coding the above-mentioned glycosylation-deficient HGF having an HGF activity, (b) DNA hybridizable under stringent conditions with DNA that is composed of a base sequence complimentary to DNA having a base sequence coding the above-mentioned glycosylation-deficient HGF having an HGF activity, or (c) DNA having a homology of at least 60% or more with DNA having a base sequence coding the above-mentioned glycosylation-deficient HGF having an HGF activity.

The phrase "deletion, substitution, addition or insertion of one to several bases" with respect to the base sequence above refers to deletion, substitution, addition or insertion of bases of a number 1 to several, which can be introduced by well-known technological methods such as a site-directed mutagenesis method or can be introduced naturally.

DNA hybridizable under stringent conditions means a DNA that can be obtained by a colony hybridization method, plaque hybridization method or southern blot hybridization method using the above DNA as a probe.

The stringent conditions mean hybridization conditions, for example, where hybridization is performed in SSC solution of about 0.1 to 2-fold concentration (SSC solution at 1-fold concentration contains 150 mM sodium chloride and 15 mM sodium citrate) at a temperature of about 65° C.

DNA having homology means DNA showing a homology of at least about 60% or more under high stringent conditions, preferably DNA having a homology of about 80% or more, more preferably DNA having a homology of about 90% or more, and furthermore preferably DNA having a homology of about 95% or more. The high stringent conditions include, for example, a sodium concentration of about 19 to 40 mM, preferably about 19 to 20 mM, and a temperature of about 50 to 70° C., preferably about 60 to 65° C. Particularly, a sodium concentration of about 19 mM and a temperature of about 65° C. are the most preferable conditions.

As the vectors which can be used in the present invention, plasmids such as pBR 322, pUC18, pUC19 (Toyobo Co. Ltd.) can be used when *Escherichia coli* is used as a host, plasmids such as pUB110 (Sigma) can be used when *Bacillus subtilis* is used as a host, and plasmids such as pYES2 (Invitrogen), pRB15 (ATCC 37062) can be used when yeast is used as a host. As the expression vector for animal cells, listed are pCAGGS and pCXN2 (Niwa H., Yamamura K. and Miyazaki J., Gene, 1991, vol. 108, p. 193 to 200, JP-A-03-168087), pcDL-SRα (Takebe Y., et al., Mol. Cell. Biol., 1988, vol. 8, p. 466-472) and the like. Additionally, bacteriophages λgt10, λgt11 (Stratagene), and a vector derived from a gene of SV40 (BRL), BPV (ATCC VR-703), retrovirus and the like are listed, however, there is no specific restriction so long as they are vectors capable of replicating and amplifying in a host.

Also regarding promoters and terminators, there is no specific restriction so long as they work in a host that is used for expression of a base sequence coding a glycosylation-deficient HGF. As the promoters, listed are trp promoter, lac promoter, recA promoter, λPL promoter, lpp promoter and the like when *Escherichia coli* is used as a host, and listed are PHO5 promoter, PGK promoter, GAP promoter, ADH promoter and the like when yeast is used as a host. When animal cells are used as a host, promoters obtained from virus genomes such as Rous sarcoma virus (virus RSV), MPSV, polyoma virus, fowlpox virus, adenovirus, bovine papilloma virus, fowl sarcoma virus, cytomegalovirus (CMV), hepatitis B virus, simian virus 40 (SV40), and vaccinia virus; metallothioneine promoter; heat shock promoter; and the like are listed. In the case of using a higher mammal host, an enhancer is preferably introduced into a vector. By introducing an enhancer, transcription increases. Listed as the enhancers are SV40 enhancer, initial promoter/enhancer of cytomegalovirus, polyoma enhancer, adenovirus enhancer and the like. As the terminator, listed are trp terminator, lpp terminator and the like when *Escherichia coli* is used as a host, listed are amyF terminator and the like when *Bacillus subtilis* is used as a host, listed are CYC1 terminator and the like when yeast is used as a host, and listed are SV40 terminator, HSV1TK terminator and the like when animal cells are used as a host. These promoters and terminators are appropriately combined depending on the host used.

An expression vector for a glycosylation-deficient HGF is introduced into a host by a competent cell method (J. Mol. Biol., 1970, vol. 53, p. 154), protoplast method (Proc. Natl. Acad. Sci. USA, 1978, vol. 75, p. 1929), calcium phosphate method (Science, 1983, vol. 221, p. 551), DEAE dextran method (Science, 1982, vol. 215, p. 166), electric pulse method (Proc. Natl. Acad. Sci. USA, 1984, vol. 81, p. 7161), in vitro packaging method (Proc. Nat. Acad. Sci. USA, 1975, vol. 72, p. 581), virus vector method (Cell, 1984, vol. 37, p. 1053), micro injection method (Exp. Cell. Res., 1984, vol. 153, p. 347) and the like, to produce a transformant.

The cell which can be used as a host is not particularly restricted, and cells derived from animals, plants, insects, and eukaryotic microorganisms, and prokaryotic microorganisms, and the like are listed. These cells may form an individual, and animal individuals, plant individuals and insect individuals may be used as a host. The animal cell may be an adherent cell or floating cell, and may be a cell producing and accumulating a glycosylation-deficient HGF in the cell, or may be a cell producing and secreting a glycosylation-deficient HGF out of the cell. As the animal cells, for example, CHO cell (Chinese hamster ovary cell), COS cell, BHK cell, mouse C127 cell and Hela cell and the like are listed. As the plant cells, for example, cells of rice, tobacco, *Arabidopsis thaliana* and the like are listed, and as the insect cell, for example, cells of Sf9, Sf21 and the like are listed. As the insect individual, for example, silk worm (Bombyx mori) is mentioned. As the prokaryotic microorganisms, *Escherichia coli*, *Bacillus subtilis* and the like are listed. As the eukaryotic microorganisms, yeasts such as *Saccharomyces cerevisiae*, *Schizosaccharomyces pombe*, *Candida boidinii*, *Pichia pastoris* and the like, and filamentous fungi such as *Aspergillus*, *Trichoderma*, *Mucor* and the like are listed. Among these, yeast, insect cell or living insect is preferable. Since the cells of the prokaryotic microorganism have no glycosylation ability, an wild-type HGF gene having glycosylation site(s) may be introduced into the cell.

The resultant transformant is cultured in an appropriate medium depending on its host for the purpose of producing an intended glycosylation-deficient HGF. The medium contains carbon sources, nitrogen sources, inorganic substances, vitamins, serum and medicaments and the like necessary for growth of the transformant. As the medium, LB medium (Nissui Pharmaceutical Co., Ltd.), M9 medium (J. Exp. Mol. Genet., Cold Spring Laboratory, New York, 1972, p. 431) and the like are listed when the host of a transformant is *Escherichia coli*, and YEPD medium (Genetic Engineering, vol. 1, Plenum Press, New York, 1979, p. 117) and the like are listed when the host is yeast. When the host is an animal cell, a modified Eagle medium (MEM medium) containing about 20% or less of fatal calf serum, Dulbecco's modified Eagle medium (DMEM medium) or RPM1640 medium (Nissui Pharmaceutical Co., Ltd.) and the like are listed. Culturing of a transformant is conducted usually at a temperature of 20 to 45° C. and pH of 5 to 8, and ventilation and stirring are conducted as required. When the host is an animal adherent cell and the like, carriers such as glass beads, collagen beads and acetyl cellulose hollow fibers are used. Culturing of a transformant can be conducted even with a medium composition or under culturing conditions other than the above compositions and conditions so long as the transformant can grow, therefore, the composition and culturing condition are not limited to the above-mentioned examples.

The glycosylation-deficient HGF thus produced in the culture supernatant of a transformant or in the transformant can be separated and purified by a combination of known methods such as salting out method, solvent precipitation method, dialysis method, ultrafiltration method, gel electrophoresis method, gel filtration chromatography, ion exchange chromatography, reverse phase chromatography, affinity chromatography and the like. Particularly, combinations of a salting out method using ammonium sulfate, S-sepharose ion chromatography, heparin sepharose affinity chromatography and phenylsepharose reverse chromatography, or combinations of a salting out method using ammonium sulfate, S-sepharose ion chromatography and anti-HGF antibody sepharose affinity chromatography are preferable and effective purification methods.

The glycosylation-deficient HGF of the present invention can also be prepared by obtaining glycosylated HGF by conventionally known methods, and subsequently by treating the HGF with an enzyme that can remove sugar chains. As the enzymes that can remove sugar chains, glycopeptidase F, glycopeptidase A and the like can be used for the purpose of removing an N-linked type sugar chain. Removal of an O-linked type sugar chain can be attained by a combination of sialidase, fucosidase and O-glycanase. The HGF from which a sugar chain is removed by enzymatic treatment can be collected as the glycosylation-deficient HGF of the present invention and purified by the above-mentioned purification method.

Further, the glycosylation-deficient HGF of the present invention can be obtained also by utilizing cell-free protein synthesis system. The cell-free protein synthesis system means a method of performing protein synthesis using DNA or mRNA coding the intended protein as a template not using a live cell, but using a cell extract that is prepared from *Escherichia coli*, rabbit reticulocyte, wheat germ and the like, or using protein synthesis factors derived from the cell extract solution. Since the cell extract solution contains molecules necessary for protein synthesis such as ribosome, tRNA, and translation factor, a protein is synthesized upon addition of an energy source such as ATP, GTP, etc. and amino acids as substrates. Instead of cell extract solution, a mixture of protein synthesis factors contained in cell extract solution may be used. In the cell-free protein synthesis system, a glycosylation-deficient HGF can be produced using, as a template, DNA or mRNA coding an HGF having glycosylation site(s), because an endoplasmic reticulum and Golgi apparatus are not contained therein. DNA or mRNA having mutation(s) introduced into glycosylation site(s) can also be used. The glycosylation-deficient HGF synthesized in the reaction solution of the cell-free protein synthesis system can be purified by the purification methods as described above.

The glycosylation-deficient HGF of the present invention obtained as described above has an activity equivalent to that of the glycosylated HGF with respect to mitogenic activity, motogenic activity and morphogenestic activity, and also has a heat stability equivalent to that of the glycosylated HGF. In addition, the glycosylation-deficient HGF of the present invention is more stable in the blood circulation than the glycosylated HGF.

The glycosylation-deficient HGF of the invention can be applied to human beings as well as to mammals (for example dog, cat, rat, mouse, rabbit, hose, cattle, sheep and guinea pig).

The medicine containing the glycosylation-deficient HGF of the invention may be used, like the wild type glycosylated HGF, for therapeutic agents for cirrhosis, therapeutic agents for renal diseases, epithelial cell proliferation promoters, anti-cancer agents, preventive agents of side effects in cancer therapy, therapeutic agents for lung injury, therapeutic agents for gastroduodenal injuries, therapeutic agents for cerebral neuropathy, preventive agents for immunosuppression side effect, collagen degradation promoters, therapeutic agents for cartilage injury, therapeutic agents for artery diseases, therapeutic agents for pulmonary fibrosis, therapeutic agents for hepatic diseases, therapeutic agents for blood coagulation malfunction, therapeutic agents for plasma hypoproteinemia, therapeutic agent for wound, neuropathy improving agents, hematopoietic cell increasing agents and hair restoration promoters. The medicine containing DNAs encoding the glycosylation-deficient HGF of the present invention may be also used for therapeutic agents of the diseases as described above.

The glycosylation-deficient HGF of the present invention is effective as a drug, and used in the form of general pharmaceutical preparation. The pharmaceutical preparation containing the glycosylation-deficient HGF of the present invention as an active ingredient can adopt various dosage forms (for example, liquid, solid, capsule and the like), and in general, the glycosylation-deficient HGF as an active ingredient is used in combination with a conventional carrier or a binder to give an injection, inhalant, suppository or oral agent, and an injection is suitable. This injection can be prepared by a normal method, and for example, can be prepared by dissolving a glycosylation-deficient HGF and a binder into a suitable solvent (for example, sterile purified water, buffer solution, physiological saline solution and the like), filtering the solution through a filter and the like for sterilization, and then filling this in a sterile vessel. The amount of the glycosylation-deficient HGF in an injection is usually adjusted from about 0.0002 to 3 (w/v %), preferably from 0.001 to 2 (w/v %). The oral drug is formulated into a dosage form such as, for example, tablet, granule, fine granule, powder, soft or hard capsule, liquid, emulsion, suspension, syrup and the like, and these preparations can be prepared by an ordinary method for preparation. The suppository can also be prepared by an ordinary method for preparation using a conventional base (for example, cacao butter, lauric butter, glycerogelatine, Macrogol, Witepsol and the like). The inhalant can also be prepared according to normal means for preparation. The amount of the glycosylation-deficient HGF in a preparation can be appropriately adjusted depending on dosage form, disease to be treated and the like.

In the formulation of a pharmaceutical preparation of the glycosylation-deficient HGF of the present invention, a stabilizer is preferably added. As the stabilizer, for example, albumin, globulin, gelatin, alanine, glycine, mannitol, glucose, dextran, sorbitol, ethylene glycol and the like are exemplified. The pharmaceutical preparation of the present invention may contain other necessary additives, for example, solvents (for example, physiological saline solution, sterile purified water, injectable water and the like), excipients (for example, fructose, D-sorbitol, glucose, starch, crystalline cellulose, dextrin and the like), binders (for example, gelatin, corn starch, tragacanth, gum arabic and the like), solubilizers (for example, lauromacrogol, Polysorbate 80, polyoxyethylene hardened castor oil 60, gum arabic, sodium benzoate and the like), antioxidants (for example, L-ascorbic acid, tocopherol, sodium edetate and the like), soothing agents (for example, benzalkonium chloride, procaine hydrochloride and the like), isotonic agents (for example, sodium chloride, glucose, D-mannitol, glycerin and the like), buffers (for example, citric acid, sodium citrate, acetic acid, sodium acetate, lactic acid, sodium hydrogenphosphate and the like), thickening agents (gum arabic, carmellose, popidone, methylcellulose and the like), preservatives (for example, methyl p-oxybenzoate, ethyl p-oxybenzoate, propyl p-oxybenzoate, chlorobutanol, benzyl alcohol, benzalkonium chloride and the like), pH adjusters (hydrochloric acid, sodium hydroxide, citric acid, acetic acid and the like), and the like.

In the case of liquid preparation, it is preferable to retain the preparation by cryopreservation, or by lyophilization and the like to remove moisture. In the case of a lyophilized preparation, injectable distilled water and the like are added before its use to redissolve the preparation.

In the case of oral preparation, it is preferable to apply a film of an enteric coating agent (for example, cellulose acetate phthalate, methacrylic acid copolymer, hydroxypropylcellulose phthalate, carboxymethylethyl cellulose and the like) to make a granule, tablet and the like, and in the case of capsule, an enteric coated capsule is preferable.

The preparation of the present invention can be administered via a suitable administration route depending on its dosage form. For example, it can be made into a form of injection and administered intravenously, intraarterially, subcutaneously, or intramuscularly, etc. The dose thereof is appropriately adjusted depending on disease, symptom, age, body weight and the like of a patient, and for example, it is usually from 0.01 mg to 500 mg, preferably from 0.05 mg to 100 mg in adults in the case of a glycosylation-deficient HGF, and once to several times administrations per day are suitable.

The DNA having a base sequence encoding the glycosylation-deficient HGF of the present invention is integrated into the vector, and is used as a gene therapy agent.

The gene therapy agent of the invention is preferably prepared as a complex of the glycosylation-deficient HGF gene and a gene carrier. Preferable gene carriers are virus vectors or cationic gene carriers. Examples of the virus vector include mouse leukemia virus vector, adenovirus vector, adeno-associated virus vector, HIV vector, herpes simplex vector, Sendai virus vector or the like. Examples of the cationic gene carrier include substances having an affinity with the gene, such as polyamino acids (e.g. polylysine, polydiamnobutyric acid, etc.) and cationic synthetic polymers (e.g. liposome, ethyleneimine, etc.).

The present invention will be further illustrated in detail by the following examples, but the invention is by no means restricted to these Examples.

Abbreviations used in the Examples have the following meanings:

HGF: hepatocyte growth factor
dHGF: 5 amino acids-deleted type hepatocyte growth factor
LB medium: Luria-Bertani medium
DMEM medium: Dulbecco's modified Eagle medium
Amp: ampicillin
FCS: fatal calf serum
NaCl: sodium chloride
BSA: bovine serum albumin
PBS: phosphate buffered saline
Tween 80: polyoxyethylene(20)sorbitan monooleate Example 1

A base sequence encoding 5 amino acids-deleted type HGF (dHGF, also named as wild type dHGF) represented by SEQ ID NO: 3 of the sequence listing was integrated into pCAGGS vector. The vector obtained (hereinafter referred to as a wild type vector) is named as pCAGGS-dHGF.

For the purpose of introducing mutations to 5 glycosylation sites (positions 289, 397, 471, 561 and 648 of SEQ ID NO: 2 in the sequence listing) present in dHGF protein, five mutagenic primers (5'-phosphorylated) shown in Table 1 were synthesized, and site-directed mutagenesis was performed using the pCAGGS-dHGF vector as a template. By this mutagenesis, Asn 289, Asn 397, Asn 561 and Asn 648 are substituted by Gln, and Thr 471 is substituted by Gly, in the amino acid sequence represented by SEQ ID NO: 2.

TABLE 1

| Primer | Sequence listing |
|---|---|
| 5'-tgc gct gac aat act atg caa gac act gat gtt cct ttg-3' | SEQ ID NO: 4 |
| 5'-ggc aaa aat tat atg ggc cag tta tcc caa aca aga tct gg-3' | SEQ ID NO: 5 |
| 5'-tgc aaa cag gtt ctc caa gtt tcc cag ctg gta tat gg-3' | SEQ ID NO: 6 |
| 5'-ggg aag gtg act ctg caa gag tct gaa ata tgt gct gg-3' | SEQ ID NO: 7 |
| 5'-ggt gat acc aca cct gga ata gtc aat tta gac cat cc-3' | SEQ ID NO: 8 |

QuickChange Multi Kit manufactured by Stratagene Co. was used for the mutagenesis. The vector containing the introduced mutations (hereinafter referred to as a mutated vector) was transformed into a competent cell of *E. coli* XL10 Gold, and Amp-resistant colonies were picked up on an LB/Amp plate. Plasmids were extracted from each clone obtained, and the intended clone was screened by analyzing a base sequence on the region coding the glycosylation-deficient HGF. A vector in which intended five mutations and no other mutation were confirmed was selected and used in the subsequent experiments. The mutated vector obtained is referred to as pCAGGS-dHGF-NG. The same operation was performed using three mutagenic primers of primer 1, primer 2 and primer 3, and a mutated vector pCAGGS-dHGF-αNG designed so as to lack three sugar chains of the α-chain was prepared. The same operation was also performed using the mutagenic primers 3 and 4, and a mutated vector pCAGGS-dHGF-βPNG designed so as to lack two sugar chains of the β-chain was prepared.

Subsequently, the wild type vector pCAGGS-dHGF and the mutated vectors pCAGGS-dHGF-NG, pCAGGS-dHGF-αNG and pCAGGS-dHGF-βNG were transfected to COS-7 cells, respectively. The COS-7 cells were cultured in a DMEM medium supplemented with 10% fetal calf serum (FCS). The culture medium of the cell was replaced with serum-free DMEM medium just before transfection. Transfection was carried out by a lipofection method using lipofectamin 2000 (manufactured by Invitrogen). The culture medium was replaced with DMEM containing 1% FCS 6 hours after the transfection, and heparin was added at a concentration of 1 μg/mL. Culturing was continued for 3 days in order to accumulate wild type dHGF or glycosylation-deficient dHGF in the culture medium. The culture media were collected 3 days after the cultivation and mixed, and the mixed medium was filtered through a 0.22 μm filter. The filtrate was preserved at −80° C. until purification. The concentrations of the wild type dHGF and glycosylation-deficient dHGFs secreted into the culture medium were analyzed by ELISA.

The above culture medium was thawed and, after filtration through a 0.22 μm filter, the filtrate was applied onto a HiTrap Heparin column (bed volume: 5 mL, manufactured by Amersham Biosciences) equilibrated with 50 mM Tris-HCl (pH 7.5), 0.01% Tween 80 and 0.3M NaCl at a flow rate of 0.6 mL/minute. The column was washed with 50 mM of Tris-HCl (pH 7.5), 0.01% Tween 80 and 0.3M NaCl, and the wild type dHGF and glycosylation-deficient dHGF were eluted by increasing the NaCl concentration to 2 M. The elution was conducted at a flow rate of 1 mL/minute, and the eluate was fractionated into tubes (2.5 mL/tube). Fractions containing the wild type dHGF or glycosylation-deficient dHGF were collected, and the buffer solution was exchanged by ultrafiltration with a buffer solution containing 50 mM Tris-HCl (pH 7.5), 0.01% Tween 80 and 0.3M NaCl. The fraction was applied onto a Mini S column (bed volume 0.8 mL, manufactured by Amersham Biosciences) at a flow rate of 0.4 mL/minute. After washing the column with 50 mM Tris-HCl (pH 7.5), 0.01% Tween 80 and 0.3 M NaCl, the wild type dHGF and glycosylation-deficient dHGFs were eluted by increasing the NaCl concentration to 1 M. The elution was performed at a flow rate of 0.4 mL/minute, and 0.4 mL each of the eluate was collected in respective tubes. The fractions containing the wild type dHGF or glycosylation-deficient dHGFs were collected, and the extent of purification was confirmed by SDS-PAGE.

The dHGF obtained by introducing the wild type vector is referred to as COS-dHGF-WT, and the glycosylation-deficient dHGFs obtained by introducing mutated vectors are referred to as COS-dHGF-NG, COS-dHGF-αNG and COS-dHGF-βNG, respectively.

The dHGF protein was also prepared using CHO cells according to the method described in JP-A-10-191991 (referred to as CHO-dHGF-WT).

The comparative results of SDS-PAGE for dHGFs and glycosylation-deficient dHGFs are shown in FIG. 1. It was confirmed that the bands of α-chain and β-chain of COS-dHGF-NG of the glycosylation-deficient dHGF were shifted respectively to positions corresponding to the molecular weights of the peptides in which the sugar-chains are deleted. While it was observed that COS-dHGF-WT has a smaller degree of glycosylation than CHO-dHGF-WT from the comparison between COS-dHGF-WT and CHO-dHGF-WT that are glycosylated (wild type) dHGFs, this may be a result from the difference of glycosylation ability between COS cells and CHO cells that were used as hosts, or from the difference of purification methods. It was confirmed that the band of α-chain of COS-dHGF-αNG, in which only the sugar chains of the α-chain were deleted, was shifted to a position corresponding to the lack of sugar chain in the α-chain. It was also confirmed that the band of β-chain of COS-dHGF-βNG, in which only the sugar chains of the β-chain were deleted, was shifted to a position corresponding to the lack of sugar chain in the β-chain.

Example 2

The mitogenic activities against rat hepatocytes of the wild type dHGF and glycosylation-deficient dHGFs obtained in Example 1 were measured.

Rat hepatocytes were separated from SD rat (age 8 weeks, male) using a collagenase perfusion method. The obtained hepatocytes were suspended in a William's E(WE) medium containing 5% FCS, and was seeded on a culture plate at a cell density of 30,000 cells/cm$^2$. The culture medium was removed 4 hours later, and was replaced with 480 μL of fresh WE medium (containing 5% FCS) to continue the culturing. After additional 20 hours, 20 μL of a sample solution containing the wild type dHGF or glycosylation-deficient dHGF was added to the medium to further continue the culturing. Twenty hours after the addition of the wild type dHGF or glycosylation-deficient dHGF, [$^3$H]-thymidine (25 Ci/mmol) was added at a concentration of 2.5 μCi/mL, and the culturing was continued for additional 6 hours. Thereafter, the cells were washed with PBS twice, followed by incubation with 10% trichloroacetic acid at 4° C. for 20 minutes. Further, the solution was replaced with fresh 10% trichloroacetic acid and the cells were kept for 10 minutes. After the cells were washed with 1 mL of H$_2$O, the cells were solubilized by incubation with 0.5 N NaOH solution at 37° C. for 30 minutes. The cell lysate was neutralized by adding 1 N HCl. The neutralized solution was treated with a cell harvester to collect cell-derived substances on a glass filter. After drying the filter, a solid scintillator (MeltiLex) was placed on the filter and the filter was heated on a hot plate. After the scintillator melted into the filter, radioactivity was measured with a β-counter (FIG. 2). The level of the radioactivity represents the amount of [$^3$H]-thymidine incorporated into the cell, indicating the amount of DNA synthesis accompanying cell proliferation. In other words, the level of the radioactivity reflects the mitogenic activity.

The glycosylation-deficient dHGF (COS-dHGF-NG) showed a mitogenic activity equivalent to that of the wild type dHGF (COS-dHGF-WT and CHO-dHGF-WT). The COS-dHGF-αNG that lacks the sugar chain of α-chain and COS-dHGF-βNG that lacks the sugar chain of β-chain also showed similar activities.

Example 3

MDCK-3B cells were suspended in DMEM (containing 10% FCS), and were seeded on a 24-well plate at a cell density of 10$^4$ cells/well (480 μL/well). A test sample (20 μL) containing the wild type dHGF or glycosylation-deficient dHGF was added to each well. The plate was incubated at 37° C. for 20 hours, and the extent of scattering was observed with a microscope (FIG. 3).

The glycosylation-deficient dHGF (COS-dHGF-NG) showed a motogenic activity equivalent to that of the wild type dHGF (COS-dHGF-WT and CHO-dHGF-WT). The COS-dHGF-αNG that lacks the sugar chain of α-chain and COS-dHGF-βNG that lacks the sugar chain of β-chain also showed similar activities.

Example 4

MDCK-3B cells were suspended in a collagen solution (Cellmatrix I-A, manufactured by Nitta Gelatin) dissolved in DMEM (containing 10% FCS) to prepare a solution with a cell density of 5,000 cells/mL. This solution (500 μL each) was added onto a 24-well plate (2,500 cells/well). After gelling collagen by incubating at 37° C. for 10 minutes, 480 μL of DMEM (containing 10% FCS) was laid on the gel, and 20 μL of a test sample containing the wild type dHGF or glycosylation-deficient dHGF was added to the well. After culturing at 37° C. for 6 days, tube formation in the gel was observed with a microscope (FIG. 4).

The glycosylation-deficient dHGF (COS-dHGF-NG) showed the same morphogenic activity as the wild type dHGFs (COS-dHGF-WT and CHO-dHGF-WT). The COS-dHGF-αNG that lacks the sugar chain of α-chain and COS-dHGF-βNG that lacks the sugar chain of β-chain also showed similar activities.

Example 5

Samples of the wild type dHGFs and glycosylation-deficient dHGFs were diluted and adjusted to a concentration of 50 μg/mL with a buffer solution containing 50 mM Tris-HCl (pH7.5), 0.01% Tween 80 and 0.3 M NaCl, and were incubated at 37° C. for 7 days in sealed vessels. Aliquots of the sample solutions were collected everyday, and each fraction was preserved at −80° C. The remaining activities of the wild type dHGFs and glycosylation-deficient dHGFs in each sampled solution were evaluated by measuring the amount of DNA synthesis of hepatocytes in a similar manner to Example 2. For measuring the activity, the sampled solution was diluted to a concentration of 125 ng/mL with PBS containing 0.5% BSA, and 20 µL aliquot of the diluted solution was added to 480 µL of a culture medium of hepatocytes to give a final concentration of 5 ng/mL.

The glycosylation-deficient dHGF (COS-dHGF-NG) showed temperature stability similar to that of the wild type dHGF (COS-dHGF-WT and CHO-dHGF-WT) (FIG. 5). The COS-dHGF-αNG that lacks the sugar chain of α-chain and COS-dHGF-βNG that lacks the sugar chain of β-chain also showed similar stabilities.

Example 6

$Na^{125}I$ (50 µCi) was added to 80 µL of a buffer solution containing 50 mM of Tris-HCl (pH 7.5), 0.01% of Tween 80 and 0.3M NaCl, and one bread of IODO-BEADS (manufactured by Pierce) was added to the solution, followed by incubation at room temperature for 5 minutes. A solution (20 µL) containing the wild type dHGF (5 µL) or glycosylation-deficient dHGF in a buffer containing 50 mM Tris-HCl (pH 7.5), 0.01% Tween 80 and 0.3 M NaCl was added to the solution above, and the dHGFs were iodinated by incubating at room temperature for 5 minutes. The iodination reaction was stopped by taking the reaction solution out of the tube, and the reaction solution taken out was subjected to gel filtration through a Sephadex G-25 column (available from Amersham Biosciences) to purify $^{125}I$-dHGF by separating from unreacted $Na^{125}I$.

$^{125}I$-dHGF with a radioactivity of 500,000 cpm was diluted with PBS containing 0.1% BSA to obtain a 100 µL solution. This solution was injected into the tail vein of ICR mouse (age 8 weeks, male). The blood was sampled at 1, 5, 15, 30, 60 and 120 minutes after the injection. The plasma was separated from the collected blood, and stability of the wild type dHGF and glycosylation-deficient dHGF in the blood circulation was evaluated by measuring the radioactivity using a gamma counter (FIG. 6).

Stability of the glycosylation-deficient dHGF (COS-dHGF-NG) in the blood circulation was improved compared with that of CHO-dHGF-WT. The COS-dHGF-WT showed an intermediate stability between COS-dHGF-NG and CHO-dHGF-WT. This may be ascribed to the fact that the sugar chain of the COS-dHGF-WT is partially deficient as shown in Example 1.

INDUSTRIAL APPLICABILITY

The glycosylation-deficient HGF of the present invention is useful as a substitute of glycosylated HGF.

The invention claimed is:
1. A glycosylation-deficient hepatocyte growth factor having no sugar chains, and having an amino acid sequence wherein the amino acids 289, 397, 561 and 648 are substituted by Gln and the amino acid 471 is substituted by Gly in the amino acid sequence represented by SEQ ID NO: 2.

```
                        SEQUENCE LISTING

<160> NUMBER OF SEQ ID NOS: 8

<210> SEQ ID NO 1
<211> LENGTH: 728
<212> TYPE: PRT
<213> ORGANISM: Homo sapiens

<400> SEQUENCE: 1

Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
```

-continued

```
                180                 185                 190
Asn Pro Glu Val Arg Tyr Glu Val Cys Asp Ile Pro Gln Cys Ser Glu
            195                 200                 205
Val Glu Cys Met Thr Cys Asn Gly Glu Ser Tyr Arg Gly Leu Met Asp
        210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
            260                 265                 270
Thr Leu Asp Pro His Thr Arg Trp Glu Tyr Cys Ala Ile Lys Thr Cys
        275                 280                 285
Ala Asp Asn Thr Met Asn Asp Thr Asp Val Pro Leu Glu Thr Thr Glu
        290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
                325                 330                 335
His Asp Met Thr Pro Glu Asn Phe Lys Cys Lys Asp Leu Arg Glu Asn
            340                 345                 350
Tyr Cys Arg Asn Pro Asp Gly Ser Glu Ser Pro Trp Cys Phe Thr Thr
        355                 360                 365
Asp Pro Asn Ile Arg Val Gly Tyr Cys Ser Gln Ile Pro Asn Cys Asp
        370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Asp Ala His
        435                 440                 445
Gly Pro Trp Cys Tyr Thr Gly Asn Pro Leu Ile Pro Trp Asp Tyr Cys
        450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
        515                 520                 525
Val Leu Thr Ala Arg Gln Cys Phe Pro Ser Arg Asp Leu Lys Asp Tyr
        530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
        595                 600                 605
```

```
Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 2
<211> LENGTH: 723
<212> TYPE: PRT
<213> ORGANISM: Homo sapiens

<400> SEQUENCE: 2

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
    195                 200                 205

Cys Asn Gly Glu Ser Tyr Arg Gly Leu Met Asp His Thr Glu Ser Gly
210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
```

-continued

```
            245                 250                 255
Asn Pro Asp Gly Gln Pro Arg Pro Trp Cys Tyr Thr Leu Asp Pro His
                260                 265                 270
Thr Arg Trp Glu Tyr Cys Ala Ile Lys Thr Cys Ala Asp Asn Thr Met
            275                 280                 285
Asn Asp Thr Asp Val Pro Leu Glu Thr Thr Glu Cys Ile Gln Gly Gln
        290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
        355                 360                 365
Val Gly Tyr Cys Ser Gln Ile Pro Asn Cys Asp Met Ser His Gly Gln
    370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
            420                 425                 430
Asn Tyr Cys Arg Asn Pro Asp Asp Ala His Gly Pro Trp Cys Tyr
        435                 440                 445
Thr Gly Asn Pro Leu Ile Pro Trp Asp Tyr Cys Pro Ile Ser Arg Cys
    450                 455                 460
Glu Gly Asp Thr Thr Pro Thr Ile Val Asn Leu Asp His Pro Val Ile
465                 470                 475                 480
Ser Cys Ala Lys Thr Lys Gln Leu Arg Val Val Asn Gly Ile Pro Thr
                485                 490                 495
Arg Thr Asn Ile Gly Trp Met Val Ser Leu Arg Tyr Arg Asn Lys His
            500                 505                 510
Ile Cys Gly Gly Ser Leu Ile Lys Glu Ser Trp Val Leu Thr Ala Arg
        515                 520                 525
Gln Cys Phe Pro Ser Arg Asp Leu Lys Asp Tyr Glu Ala Trp Leu Gly
    530                 535                 540
Ile His Asp Val His Gly Arg Gly Asp Glu Lys Cys Lys Gln Val Leu
545                 550                 555                 560
Asn Val Ser Gln Leu Val Tyr Gly Pro Glu Gly Ser Asp Leu Val Leu
                565                 570                 575
Met Lys Leu Ala Arg Pro Ala Val Leu Asp Asp Phe Val Ser Thr Ile
            580                 585                 590
Asp Leu Pro Asn Tyr Gly Cys Thr Ile Pro Glu Lys Thr Ser Cys Ser
        595                 600                 605
Val Tyr Gly Trp Gly Tyr Thr Gly Leu Ile Asn Tyr Asp Gly Leu Leu
    610                 615                 620
Arg Val Ala His Leu Tyr Ile Met Gly Asn Glu Lys Cys Ser Gln His
625                 630                 635                 640
His Arg Gly Lys Val Thr Leu Asn Glu Ser Glu Ile Cys Ala Gly Ala
                645                 650                 655
Glu Lys Ile Gly Ser Gly Pro Cys Glu Gly Asp Tyr Gly Gly Pro Leu
            660                 665                 670
```

```
Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
        690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 3
<211> LENGTH: 2172
<212> TYPE: DNA
<213> ORGANISM: Homo sapiens

<400> SEQUENCE: 3
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa atcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgttttttgat aaagcaagaa acaatgcct ctggttcccc     300 ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta gagtggcat caaatgtcag ccctggagtt ccatgatacc acacgaacac     480
agctatcggg gtaaagacct acaggaaaac tactgtcgaa atcctcgagg ggaagaaggg     540
ggaccctggt gtttcacaag caatccagag gtacgctacg aagtctgtga cattcctcag     600
tgttcagaag ttgaatgcat gacctgcaat ggggagagtt atcgaggtct catggatcat     660
acagaatcag gcaagatttg tcagcgctgg gatcatcaga caccacaccg gcacaaattc     720
ttgcctgaaa gatatcccga caagggcttt gatgataatt attgccgcaa tcccgatggc     780
cagccgaggc catggtgcta tactcttgac cctcacaccc gctgggagta ctgtgcaatt     840
aaaacatgcg ctgacaatac tatgaatgac actgatgttc ctttggaaac aactgaatgc     900
atccaaggtc aaggagaagg ctacaggggc actgtcaata ccatttggaa tggaattcca     960
tgtcagcgtt gggattctca gtatcctcac gagcatgaca tgactcctga aaatttcaag    1020
tgcaaggacc tacgagaaaa ttactgccga atccagatg gtctgaatc accctggtgt    1080 tttaccactg atccaaacat ccgagttggc tactgctccc aaattccaa ctgtgatatg    1140 tcacatggac aagattgtta tcgtgggaat ggcaaaaatt atatgggcaa cttatcccaa    1200
acaagatctg gactaacatg ttcaatgtgg gacaagaaca tggaagactt acatcgtcat    1260
atcttctggg aaccagatgc aagtaagctg aatgagaatt actgccgaaa tccagatgat    1320
gatgctcatg gaccctggtg ctacacggga aatccactca ttccttggga ttattgccct    1380
atttctcgtt gtgaaggtga taccacacct acaatagtca atttagacca tcccgtaata    1440
tcttgtgcca aaacgaaaca attgcgagtt gtaaatggga ttccaacacg aacaaacata    1500
ggatggatgg ttagtttgag atacagaaat aaacatatct gcggaggatc attgataaag    1560
gagagttggg ttcttactgc acgacagtgt ttcccttctc gagacttgaa agattatgaa    1620
gcttggcttg gaattcatga tgtccacgga agaggagatg agaaatgcaa acaggttctc    1680
aatgtttccc agctggtata tggccctgaa ggatcagatc tggttttaat gaagcttgcc    1740
aggcctgctg tcctggatga ttttgttagt acgattgatt tacctaatta tggatgcaca    1800
```

-continued

```
attcctgaaa agaccagttg cagtgtttat ggctggggct acactggatt gatcaactat    1860
gatggcctat tacgagtggc acatctctat ataatgggaa atgagaaatg cagccagcat    1920
catcgaggga aggtgactct gaatgagtct gaaatatgtg ctggggctga aaagattgga    1980
tcaggaccat gtgaggggga ttatggtggc ccacttgttt gtgagcaaca taaaatgaga    2040
atggttcttg gtgtcattgt tcctggtcgt ggatgtgcca ttccaaatcg tcctggtatt    2100
tttgtccgag tagcatatta tgcaaaatgg atacacaaaa ttattttaac atataaggta    2160
ccacagtcat ag                                                        2172
```

<210> SEQ ID NO 4
<211> LENGTH: 39
<212> TYPE: DNA
<213> ORGANISM: Artificial
<220> FEATURE:
<223> OTHER INFORMATION: Synthetic Construct

<400> SEQUENCE: 4

```
tgcgctgaca atactatgca agacactgat gttcctttg                            39
```

<210> SEQ ID NO 5
<211> LENGTH: 41
<212> TYPE: DNA
<213> ORGANISM: Artificial
<220> FEATURE:
<223> OTHER INFORMATION: Synthetic Construct

<400> SEQUENCE: 5

```
ggcaaaaatt atatgggcca gttatcccaa acaagatctg g                         41
```

<210> SEQ ID NO 6
<211> LENGTH: 38
<212> TYPE: DNA
<213> ORGANISM: Artificial
<220> FEATURE:
<223> OTHER INFORMATION: Synthetic Construct

<400> SEQUENCE: 6

```
tgcaaacagg ttctccaagt ttcccagctg gtatatgg                             38
```

<210> SEQ ID NO 7
<211> LENGTH: 38
<212> TYPE: DNA
<213> ORGANISM: Artificial
<220> FEATURE:
<223> OTHER INFORMATION: Synthetic Construct

<400> SEQUENCE: 7

```
gggaaggtga ctctgcaaga gtctgaaata tgtgctgg                             38
```

<210> SEQ ID NO 8
<211> LENGTH: 38
<212> TYPE: DNA
<213> ORGANISM: Artificial
<220> FEATURE:
<223> OTHER INFORMATION: Synthetic Construct

<400> SEQUENCE: 8

```
ggtgatacca cacctggaat agtcaattta gaccatcc                             38
```